(12) United States Patent
Bruce et al.

(10) Patent No.: US 9,682,103 B1
(45) Date of Patent: Jun. 20, 2017

(54) ADMINISTRATION OF A POLY-OXYGENATED METAL HYDROXIDE TO REDUCE THE PROLIFERATION OF CARCINOMA CELLS

(71) Applicant: Baylor University, Waco, TX (US)

(72) Inventors: Erica D. Bruce, Hewitt, TX (US); Christie Sayes, McGregor, TX (US); John W. Woodmansee, Jr., Frisco, TX (US)

(73) Assignee: Baylor University, Waco, TX (US)

( * ) Notice: Subject to any disclaimer, the term of this patent is extended or adjusted under 35 U.S.C. 154(b) by 0 days.

(21) Appl. No.: 15/346,580

(22) Filed: Nov. 8, 2016

Related U.S. Application Data

(63) Continuation of application No. 15/183,403, filed on Jun. 15, 2016, now Pat. No. 9,649,335.

(60) Provisional application No. 62/315,524, filed on Mar. 30, 2016.

(51) Int. Cl.
  *A61K 33/08* (2006.01)
  *A61K 9/00* (2006.01)
  *C01F 7/02* (2006.01)

(52) U.S. Cl.
  CPC ............ *A61K 33/08* (2013.01); *A61K 9/0019* (2013.01); *C01F 7/02* (2013.01)

(58) Field of Classification Search
  None
  See application file for complete search history.

(56) References Cited

U.S. PATENT DOCUMENTS

| 4,032,623 A | 6/1977 | Merkl |
| 4,093,707 A | 6/1978 | Merkl |
| 2006/0233713 A1* | 10/2006 | MacQueen ............ A61K 31/28 424/9.34 |
| 2015/0086649 A1* | 3/2015 | Walsh .................... A61K 33/08 424/690 |

FOREIGN PATENT DOCUMENTS

| CN | WO 2014139456 A1 * | 9/2014 | ............ A61K 33/08 |

OTHER PUBLICATIONS

American Cancer Society, When someone you know has cancer, 2015, pp. 1-3 ([retrieved from on-line website: http://www.cancer.org/treatment/understandingyourdiagnosis/talkingaboutcancer/whensomeoneyouknowhascancer/when-somebody-you-know-has-cancer-cancer-treatment-questions], last visit Dec. 12, 2016).*

(Continued)

*Primary Examiner* — Ernst V Arnold
*Assistant Examiner* — Kyung Sook Chang
(74) *Attorney, Agent, or Firm* — Robert C. Klinger

(57) ABSTRACT

A method of treating a condition of a mammal, including a human individual and an animal, by intravenously administering a therapeutically effective amount of a poly-oxygenated metal hydroxide. In some embodiments, the poly-oxygenated metal hydroxide is an aluminum poly-oxygenated hydroxide, such as Ox66™. The poly-oxygenated metal hydroxide may have particles having a diameter of less than or equal to 1 um, and specifically having a diameter of less than or equal to 100 nm. The poly-oxygenated metal hydroxide may be 75-90% colloid or crystalline solution with 10-25% addition of poly-oxygenated metal hydroxide particles.

8 Claims, 11 Drawing Sheets

(56) References Cited

OTHER PUBLICATIONS

Consumer updates, "Hyperbaric Oxygen Therapy" ([retrieved from on-line website: http://www.fda.gov/downloads/ForConsumers/ConsumerUpdates/UCM366015.pdf, last visit Dec. 2, 2012]).*

Synonyms ([retrieved from on-line website http://www.thegoodscentscompany.com/data/rw1538901.html, last visit Dec. 2, 2016).*

Cancer Fighting Strategies ([retrieved from on-line website: https://web.archive.org/web/20061113093142/http://www.cancerfightingstrategies.com/print.html, last visit Dec. 2, 2016]).*

Rasma Cheesan, "Bioavailability, Bioequivalence, and Drug Selection", chapter 8, Basic Pharmacokinetics, 1996, pp. 8.1-8.17.*

Zips et al., "New Anticancer Agents: In Vitro and In Vivo Evaluation", In vivo 19:1-8 (2005).*

Article, "Lead hydroxide", Cas No. 19783-14-3 ([retrieved on line website: https://echa.europa.eu/registration-dossier/-/registered-dossier/2047/2/1, last visit Dec. 2, 2016]).*

Article, "Sodium Hydroxide" ([retrieved from on-line website: http://www.health-report.co.uk/sodium_hydroxide.htm, last visit Dec. 2, 2016]).*

Jack Woodmansee, Class of 1952 of Culver Military Academy, Oct. 10, 2013 ([retrived from on-line website:https://alumni.culver.org/document.doc?id=517&chid=63]).*

* cited by examiner

Control 0.25mg/ml

ADMINISTRATION OF A POLY-OXYGENATED METAL HYDROXIDE TO REDUCE THE PROLIFERATION OF CARCINOMA CELLS

CLAIM OF PRIORITY

This application is a Continuation of and claims priority under 35 U.S.C. Section 119 of U.S. patent application Ser. No. 15/183,403 filed Jun. 15, 2016, entitled INTRAVENOUS ADMINISTRTION OF AN OXYGEN-ENABLE FLUID, which application claims priority of U.S. patent application Ser. No. 62/315,524 entitled OXYGEN -ENABLED RESUSCITATIVE FLUID filed Mar. 30, 2016, the teachings of which are incorporated herein by reference in their entirety.

TECHNICAL FIELD

This disclosure is directed to an oxygen-enabled resuscitative fluid, and methods for use in mammals including humans and animals.

BACKGROUND

When blood is lost, the chief immediate need is to cease further blood loss followed by replacing the lost blood volume. This critical need is important for allowing the remaining red blood cells to oxygenate body tissue albeit at a reduced capacity. When the body detects the lower hemoglobin levels, from extreme blood loss, compensatory mechanisms begin. There are currently no resuscitative fluids that provide oxygen to hypoxic cells and tissues following major blood loss.

Oxygen therapeutics have traditionally been categorized as either hemoglobin -based oxygen carriers (HBOCs) or perfluorocarbons (PFCs). Unlike blood, HBOCs and PFCs do not require blood typing, have a long shelf life, do not transmit blood borne diseases, and in most cases do not need refrigeration. Despite these promising attributes the widespread utility of HBOCs and PFCs has been limited by concerns regarding hypertension from systemic arteriolar constriction and leukocyte activation, respectively.

SUMMARY

A method of treating, a condition, of a mammal, including a human individual and an animal, comprising intravenously administering the mammal a therapeutically effective amount of a poly-oxygenated metal hydroxide.

In some embodiments, the poly-oxygenated metal hydroxide is an aluminum poly-oxygenated hydroxide, such as Ox66™. The poly-oxygenated metal hydroxide may have particles having a diameter of less than or equal to 1 um, and specifically having a diameter of less than or equal to 100 nm. The poly-oxygenated metal hydroxide is 75-90% colloid or crystalline solution with 10-25% addition of poly-oxygenated metal hydroxide particles. The poly-oxygenated metal hydroxide may have a concentration range of 0.1 mg/l to 1000 mg/l. The poly-oxygenated metal hydroxide may have particles that are surface modified.

In one embodiment, the condition is a depletion of hemoglobin in the mammal, wherein the poly-oxygenated metal hydroxide acts is an oxygen resuscitative fluid.

DESCRIPTION OF EXEMPLARY EMBODIMENTS

Figure 1:
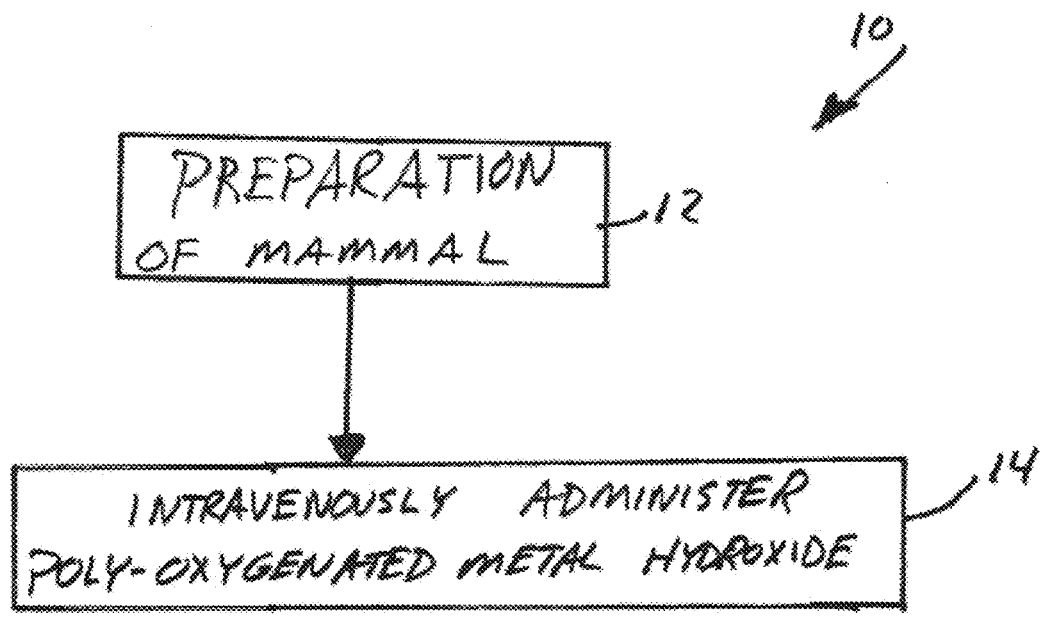
FIG. 1 illustrates a method of intravenously administering a mammal a therapeutically effective amount of a poly-oxygenated metal hydroxide in accordance with this disclosure.
Figure 2A:
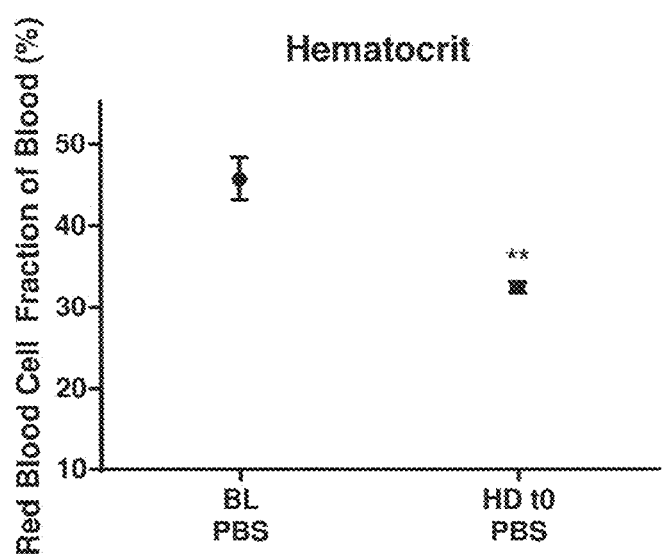
FIGS. 2A-2D are diagrams illustrating systemic characteristics of 50% isovolemic hemodilution, including hematocrit, heart rate, mean arterial pressure, and pulse pressure Measurements were taken immediately prior to (BL) and following (HD t0) hemodilution.
Figure 2B:
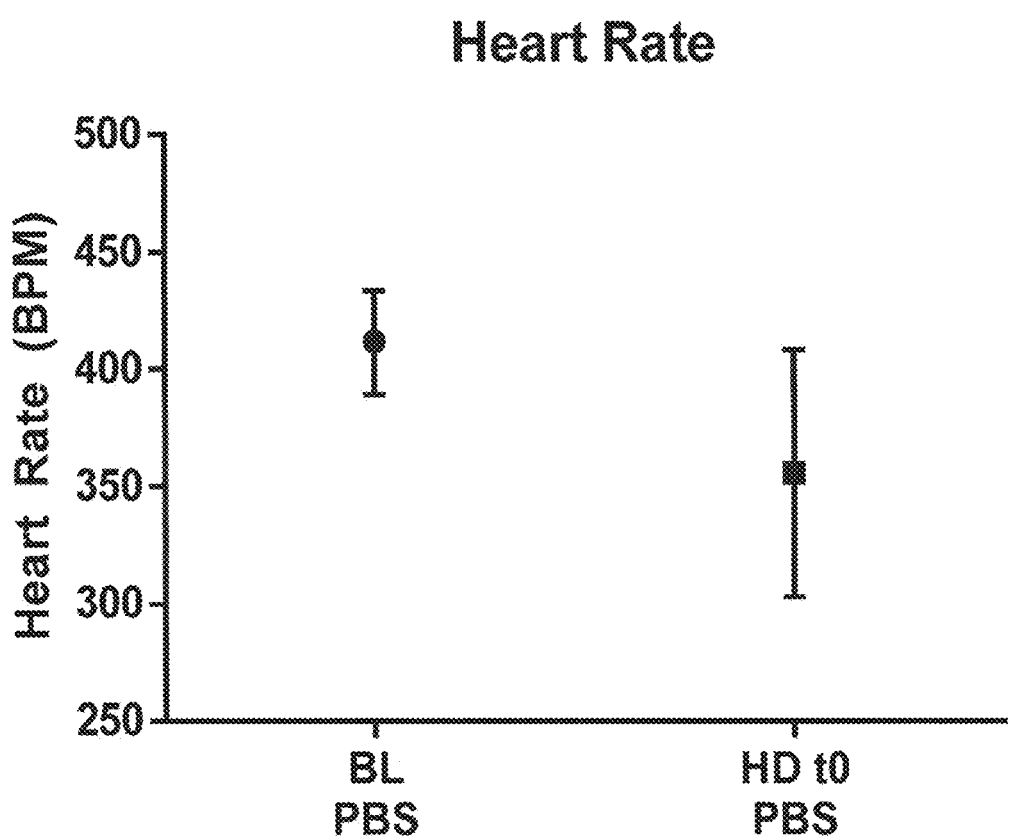
Figure 2C:
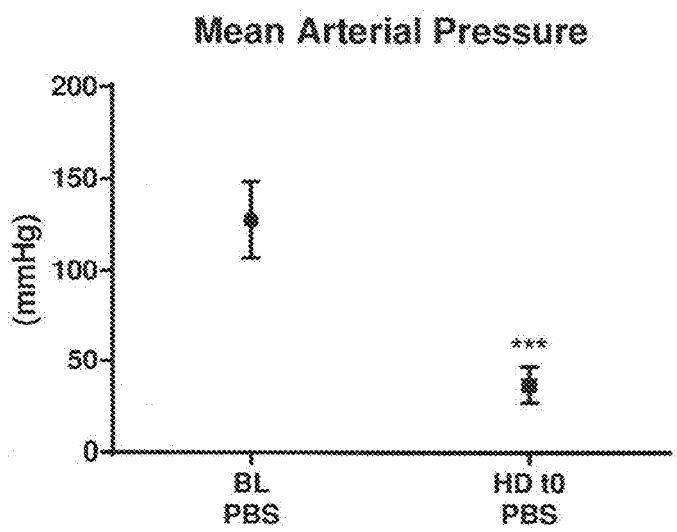
Figure 2D:
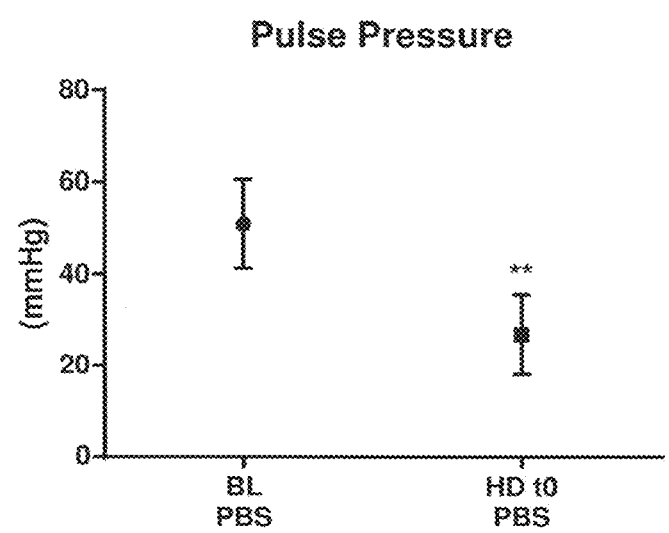

The following description of exemplary embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in. a position to receive treatment. However, as should be recognized by those skilled in the art, this frame of reference is merely a descriptive expedient rather than a strict prescription.

Despite what is known from physiological principles, there is no practice-based evidence to suggest colloid solutions offer substantive advantages over crystalloid solutions with respect to hemodynamic effects. In addition, there is no evidence to recommend the use of other semisynthetic colloid solutions. Balanced salt solutions are reasonable initial resuscitation fluids, although there is limited practice-based evidence regarding their safety and efficacy. Additionally, the safety of hypertonic solutions has not been established. Ultimately, the selection of the specific resuscitative fluid should be based on indications, contraindications, and potential toxic effects in order to maximize efficacy and minimize toxicity. In addition, the capability of a resuscitative fluid to carry oxygen, as well as to maximize efficacy and minimize toxicity, is desperately needed.

According to this disclosure, there is a significant therapeutic benefit to intravenously oxygenate blood of a human individual and animal, collectively mammals, and create a more effective resuscitative fluid using a poly-oxygenated metal hydroxide, and particularly nano-sized poly -oxygenated aluminum hydroxide, such as Ox66™ oxygen carrying particles manufactured by Hemotek, LLC of Plano, Tex. Ox66™ is an oxygen carrying powder that contains about 66% oxygen, and includes a true clathrate that is a latticelike structure that provides large areas capable of capturing and holding oxygen. This disclosure significantly increases tissue oxygenation of the mammal known as $PO_2$. In certain applications of Ox66™, the $PO_2$ levels of a hemo-diluted mammal can exceed baseline. Fluid resuscitation with colloid and crystalloid solutions is a global intervention in acute medicine, and while the selection and ultimate use of resuscitation fluids is based on physiological principles, clinician preference determines clinical use. Studies have shown that Ox66™ is to not create any negative effects in toxicology studies where Ox66™ was either injected or gavaged.

With enough blood loss, like in amputations and other military trauma situations, red blood cell levels drop too low for adequate $PO_2$ tissue oxygenation, even if volume expanders maintain circulatory volume. In these situations, the only currently available alternatives are blood transfusions, packed red blood cells, or a novel oxygen-enabled resuscitative fluid according to this disclosure.

This disclosure provides a novel oxygen-enabled resuscitative fluid that can effectively oxygenate mammal tissues and provide essential elements to protect and save critical cells and tissues, and the mammal itself. This disclosure is desperately needed on the battlefield, as well as in civilian trauma cases. One exemplary formulation consists of 75-90% colloid or crystalline solutions with 10-25% addition of nano-sized Ox66™ particles, resulting in concertation ranges of 0.1 mg/l to 1000 mg/l. For use as resuscitative fluid, ideal sizes of the Ox66™ particles may be between 10 nm to 100 μm in size, depending on the treatment. To avoid immune suppression, the diameter of the Ox66™ particles should ideally be less than 100 nm, and preferably less than 70 nm as these particle sizes have been proven to maximize efficacy and minimize toxicity.

As shown in FIG. 1, this exemplary embodiment comprises a method 10 of intravenously administering a mammal a therapeutic amount of a composition including a poly-oxygenated metal hydroxide, such as a human individual, or an animal. The poly-oxygenated metal hydroxide composition may comprise a poly-oxygenated aluminum hydroxide, such as Ox66™ particles. One method can include administration of a therapeutically effective resuscitative fluid to increase $PO_2$ in the mammal. Another method can include administration of a therapeutically effective composition to treat a condition of a mammal. The method comprises preparing a mammal at step 12, such as preparing a site on the mammal for receiving a catheter, and intravenously administering a poly-oxygenated metal hydroxide composition at step 14, such as using a catheter. Various methods and treatments are detailed as follows.

Study

A clinical study was performed to ascertain the efficacy of a poly-oxygenated metal hydroxide in a mammal, comprising Ox66™ particles, and the details of the study and results are included. For this study, Particle Size A diameter is 100 um and Particle Size B diameter is 10 μm.

In this study, male Sprague-Dawley rats underwent a 50% blood volume isovolemic hemodilution exchange with either Ox66™ or phosphate buffered saline (PBS; volume control), since Ox66™ was suspended in PBS. Isovolemic hemodilution is the reduction of red blood cells (hematocrit) with an equal volume of hemodiluent, i.e., crystalloids, colloids or oxygen therapeutics.

The withdrawal/infusion rate was 2.0 $mlxmin^{-1}xkg^{-1}$ and performed through a cannulated carotid artery and jugular vein. Systemic measurements were recorded via a cannulated femoral artery that was connected to a pressure transducer (MP150; Biopac Systems, Inc, Goleta, Calif.), while microcirculatory parameters were collected through phosphorescence quenching and intravital microscopic examination of the exteriorized spinotrapezius muscle. Compared to baseline, a 50% blood volume exchange with either hemodiluent caused a reduction in heart rate, blood pressure, arterial diameter and ISF $PO_2$ in all animals. However, Ox66™ animals demonstrated an improvement in ISF $PO_2$ compared to PBS animals. This finding demonstrates that Ox66™ both transports and releases oxygen to the peripheral microcirculation.

Animals
Male Sprague Dawley rats (250-300 g) Anesthetics
Isoflurane (induction)
Alfaxalone continuous rate of infusion)
   Surgical Preparation
Vessels and tracheal cannulation
Spinotrapezius muscle exteriorized
   Systemic Parameters
BIOPAC MP150 (real-time analysis)
   Tissue Oxygenation
Phosphorescence Quenching Microscopy
Palladium porphyrin (R0) probe distributed into interstitium.
Phosphorescence decay curve captured and fit to standard curve for translation to $P_{ISF}$ $O_2$ in mmHg.
   Hemodilution (HD)
Baseline parameters collected
50% isovolemic exchange of blood with test solution at 2.0 ml/kg/min
Post-HD parameters collected
Animals observed for 2 h post-HD
   Hemodiluents
Phosphate Buffered Saline (PBS)
Ox66™ Size A [1×]
Ox66™ Size A [10×]
Ox66™ Size B [1×]
Ox66™ Size B [10×]

FIG. 2 shows systemic characteristics of 50% isovolemic hemodilution. Measurements were taken immediately prior to (BL) and following (HD t0) hemodilution. The volume exchange of whole blood with PBS (vehicle volume control) resulted in significant reductions in hematocrit, mean arterial pressure, and pulse pressure. The reduction in heart rate lacked statistical strength. $p<0.01$, * $p<0.001$.

Figure 3:
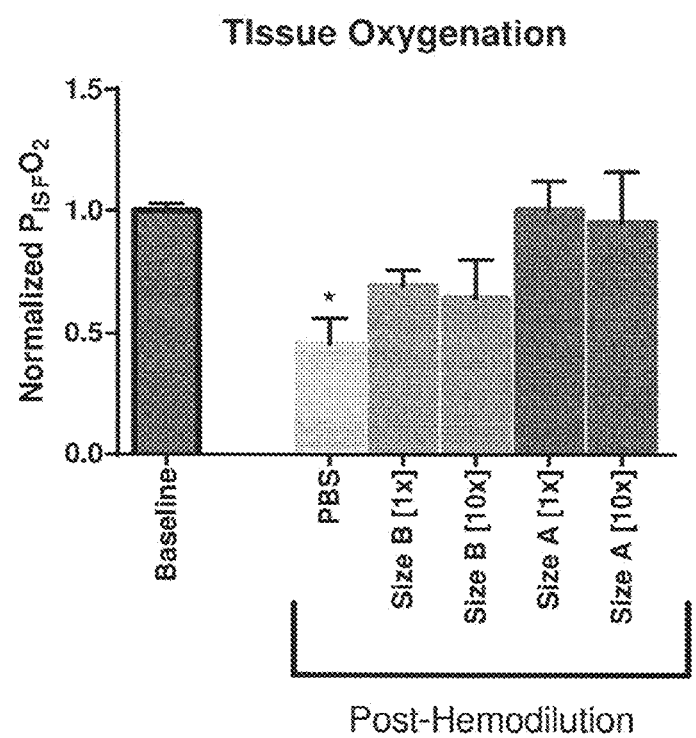
FIG. 3 shows tissue oxygenation ($P_{ISF}$ $O_2$) following 50% volume replacement. All $P_{ISF}$ $O_2$ values (mmHg) were normalized to baseline (BL) for ease of comparison.

FIG. 3 shows tissue oxygenation ($P_{ISF}$ $O_2$) following 50% volume replacement. All $P_{ISF}$ $O_2$ values (mmHg) were normalized to baseline (BL) for ease of comparison. Ox66™ compounds were suspended in PBS, which was used as a vehicle volume control. Size A was larger than B and trended towards higher oxygen delivery. Both sizes were assessed at 1× and 10× concentrations, but failed to show a concentration dependence of $P_{ISF}$ $O_2$ in this range. *$p<0.05$ vs BL.

Figure 4A:
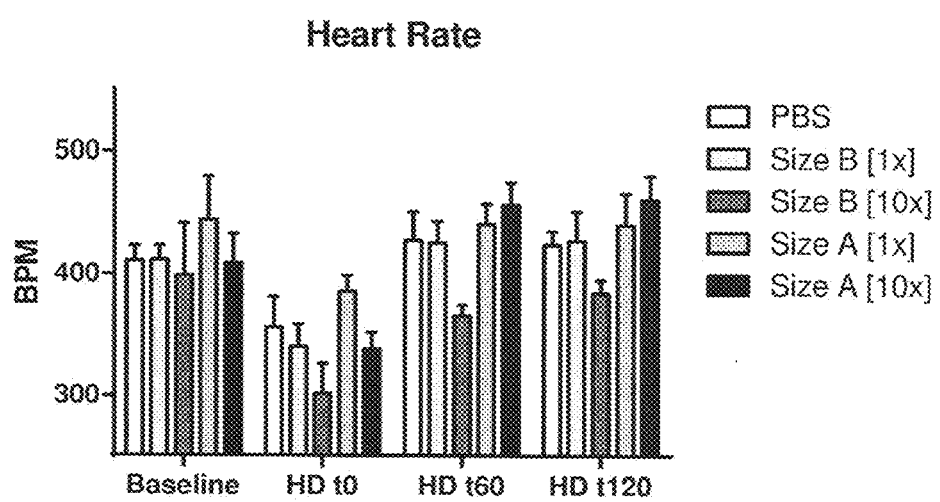
FIGS. 4A and 4B show systemic parameters including heart rate and mean arterial pressure following isovolemic hemodilution with test solutions.
Figure 4B:
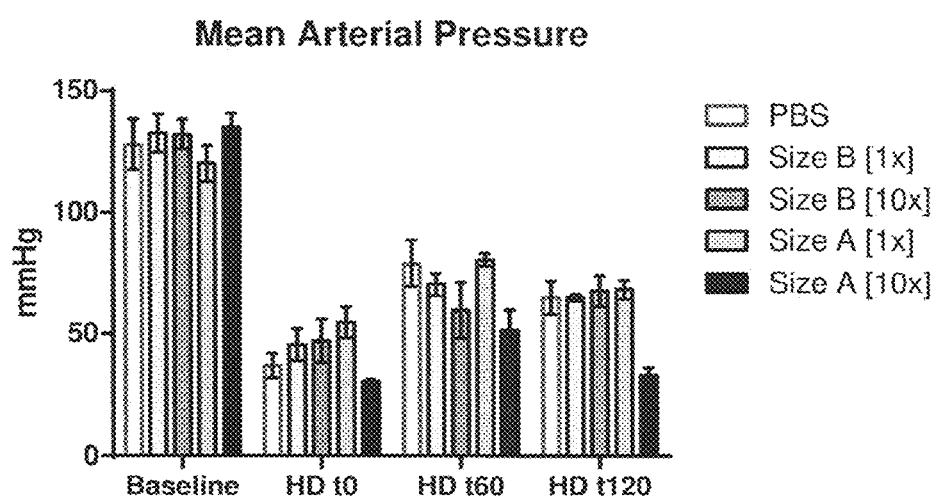

FIG. 4 shows systemic parameters following isovolemic hemodilution with test solutions. HD=Hemodilution; tn=time point in minutes following hemodilution. Heart rates generally followed the scheme of slowing down by HD t0 and then returning to baseline by t60. Mean arterial pressure remained low, but stable following hemodilution with the exception of Size A at 10× concentration. Statistical tests were not performed due to low sample sizes (N=2-4).

Figure 5:
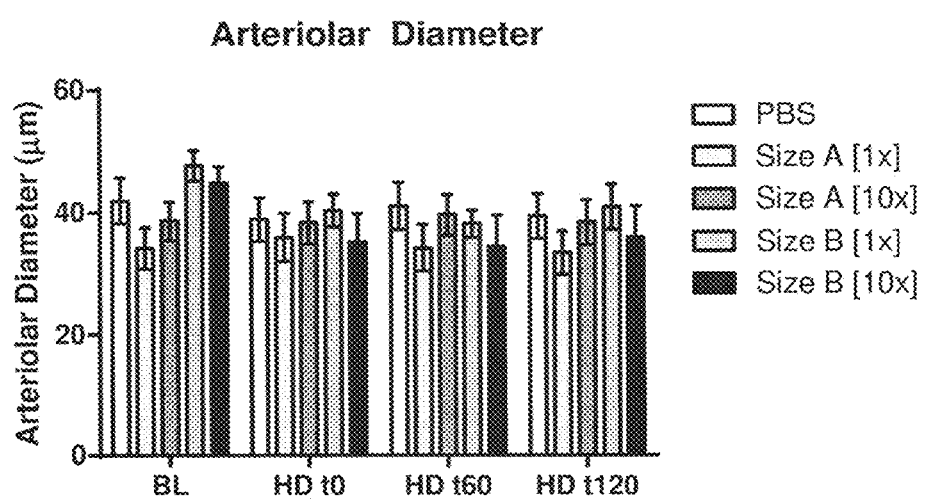
FIG. 5 shows arteriolar luminal diameters. Arterioles included were smaller than 60 microns at baseline.

FIG. 5 shows arteriolar luminal diameters. Arterioles included were smaller than 60 microns at baseline.

Summary

The '50% Isovolemic Hemodiltuion' model produces a good reduction in systemic cardiovascular parameters and tissue oxygenation to assess therapeutic potential of interventions.

Ox66™ is capable of carrying and delivering oxygen to hypoxic peripheral tissues.

Administering Surface Modified Ox66™ Particles

In an exemplary embodiment, the administered Ox66™ particles may be surface modified for specific therapeutic uses such as time release, PEGylation, growth factor modification, antibacterial, antimicrobial, protein modification, and enzymes.

Treatment of Traumatic Brain Injury (TBI), Strokes, and CTE

To achieve microcirculation in mammals, such as to treat TBI and strokes, the Ox66™ particles preferably have a diameter of less than 10 nm to pass the blood brain barrier (BBB). The upper limit of pore size enabling passive flow across the BBB is usually <1 nm; however, particles having a diameter of several nanometers can also cross the BBB via carrier-mediated transport using specialized transport proteins. Alternatively, receptor-mediated transport can act as an "escort" for larger particles. This exemplary embodiment comprising intravenously administering a therapeutic amount of a composition including Ox66™ particles having a diameter of less than 10 nm is therapeutically effective in treating a mammal with TBI and BBB. This is an extraordinary accomplishment, and can revolutionize the treatment of not only TBI and BBB, but also other brain conditions/injury including Chronic Traumatic Encephalopathy (CTE), which is a progressive degenerative disease of the brain found in athletes, military veterans, and others with a history of repetitive brain trauma.

Treatment Diabetes

To achieve microcirculation in mammals to treat Diabetes, this exemplary embodiment comprises intravenously administering to a mammal a therapeutic amount of a composition including Ox66™ particles as a fluid that is therapeutically effective to increase $PO_2$ in the mammal, such as a human individual, or an animal, to reduce the effects of Diabetes.

Treatment of Cancer

To treat cancer in mammals, this exemplary embodiment comprises intravenously administering to a mammal a therapeutic amount of a composition including Ox66™ particles as a fluid that is therapeutically effective to reduce the effects of, or eliminate, cancer in the mammal, such as a human individual, or an animal.

Study

Figure 6:
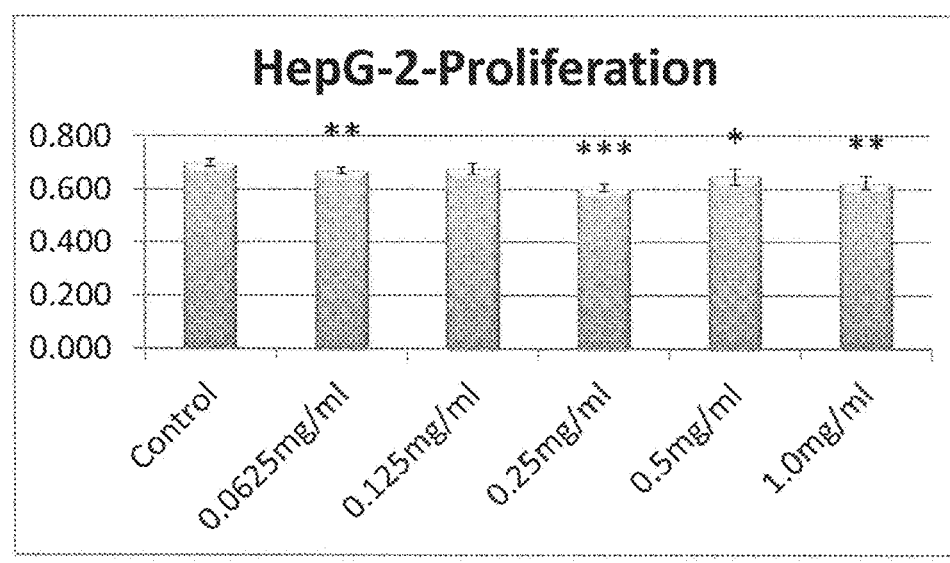
FIG. 6 shows the proliferation of hepatocarcinoma cells (HEPG-2) significantly reduced following administration with various concentrations of Ox66™.

The proliferation of hepatocarcinoma cells (HEPG-2) was significantly reduced following administration with various concentrations of Ox66™ as shown in FIG. 6.

Figure 7A:
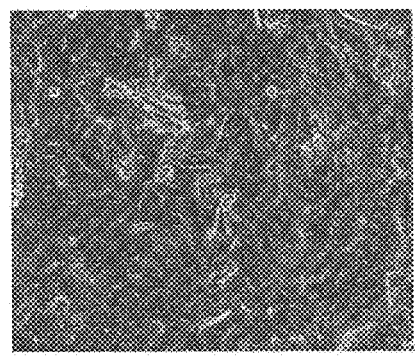
FIG. 7A and FIG. 7B illustrate images of cells HEPG-2 cells prior to dosing and after dosing, respectively.
Figure 7B:
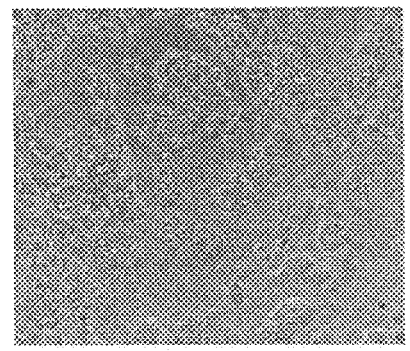

Images shown in FIG. 7A and FIG. 7B illustrate cells HEPG-2 cells prior to dosing and after dosing, respectively.

Erectile Dysfunction

To achieve the treatment of erectile dysfunction in mammals, this exemplary embodiment comprises intravenously administering to a mammal a therapeutic amount of a composition including Ox66™ particles that is therapeutically effective to increase oxygenated blood flow thus mitigating physical dysfunction in the mammal, such as a human individual, or an animal, to reduce the effects of erectile dysfunction. In another embodiment, the Ox66™ particles could be embodied in a tablet or capsule form and administered orally.

Sickle Cell Anemia

To achieve the treatment of sickle cell anemia in mammals, this exemplary embodiment comprises intravenously administering to a mammal a therapeutic amount of a composition including Ox66™ particles (~0.07 μm) that is therapeutically effective to increase oxygenated blood flow thus mitigating dysfunction in the mammal, such as a human individual, or an animal, to reduce the effects of sickle cell anemia. In another embodiment, the Ox66™ particles could be embodied in a tablet or capsule form and administered orally. In sickle cell anemia, the red blood cells become rigid and tacky and are shaped like sickles hence the name of the disease. These irregularly shaped "sickle" cells do not move through small blood vessels, resulting in slowing or blockage of blood flow and oxygen to parts of the body. This embodiment of Ox66™ particles could oxygenated the body in a crisis and act as an alleviation strategy for sickle cell anemia.

Bronchopulmonary Dysplasia (BPD)

To treat bronchopulmonary dysplasia in mammals, this exemplary embodiment comprises intravenously administering to a mammal a therapeutic amount of a composition including Ox66™ particles as fluid that is therapeutically effective to reduce the effects of, or eliminate, BPD in the mammal, such as a human individual, or an animal. A critical problem facing preterm infants is adequate lung function. Premature babies can have strokes, chronic lung disease and potential brain damage due to small, fragile blood vessels, and pressurized oxygen required after birth to keep the lungs functional. There is a need for an alternative oxygen therapy that mitigates the aforementioned risks. These preemies frequently encounter complications such as chronic lung disease—sometimes called bronchopulmonary dysplasia (BPD). BPD can occur because the infants still have some inflammation in their lungs and may require extra oxygen or medications to help them breathe comfortably. There are several hyper-oxygenated associated illnesses that a preterm infant will suffer such as retinopathy of prematurity (ROP), periventricular leukomalacia, cerebral palsy, and, the previously mentioned bronchopulmonary dysplasia (BPD), to name a few. Administration of Ox66™ provides alternative oxygen delivered by less invasive means yet supplying oxygen to the preterm infant.

Alzheimer's Disease (AD)

To treat Alzheimer's disease in mammals, this exemplary embodiment comprises intravenously administering to a mammal a therapeutic amount of a composition including Ox66™ particles as a fluid that is therapeutically effective to reduce the effects of, or eliminate, AD in the mammal, such as a human individual, or an animal. Alzheimer's disease (AD) is classified as a neurodegenerative disorder. The cause and progression of the disease are not well understood. AD is associated with hallmarks of plaques and tangles in the brain. Current treatments only help with the symptoms of the disease and there are no available treatments that stop or reverse the progression of the disease. As of 2012, more than 1,000 clinical trials have been or are being conducted to test various compounds in AD. There is currently no approved drug therapy for AD that will stop or reverse the progression of the disease. There is a clear link between low oxygen levels in the brain and Alzheimer's disease, but the exact mechanisms behind this are not yet fully understood (Alzheimer's Society, Proceedings of the National Academy of Sciences). A healthy brain needs a good supply of oxygen. A disruption of the blood flow through or to the brain causes low oxygen levels. When there is damage or a blockage, or the blood supply itself is low in oxygen then insufficient oxygen will be delivered to the brain cells. Ox66™ offers the potential of micrometer sized (~0.07 μm) particles increasing oxygen delivery to the brain. With this offloading of oxygen, there is significant potential to mitigate the development and/or the progression of AD.

Autism

To treat autism in mammals, this exemplary embodiment comprises intravenously administering to a mammal a therapeutic amount of a composition including Ox66™ particles as a fluid that is therapeutically effective to reduce the effects of, or eliminate, autism in the mammal, such as a human individual, or an animal. Several problems that crop up during labor and shortly after birth appear to increase a child's risk for developing autism. A recent study published in the Journal of Pediatrics, a review of 40 studies published before April 2007, looked at a host of circumstances that may affect babies during labor and delivery. It found 16 circumstances that appear to be tied to a significantly increased risk that a child would develop autism later in life. Researchers note that many of these complications tend to occur together in difficult or high-risk deliveries, making it difficult to finger a single suspect. But broadly, researchers note, they seem to be related to oxygen deprivation and growth retardation.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A method of treating a human individual, comprising: administering a therapeutically effective amount of a poly-oxygenated aluminum hydroxide composition to a human individual to reduce a proliferation of heptocarcinoma cells (HEPG-2), wherein the poly-oxygenated aluminum hydroxide composition comprises a clathrate containing free oxygen gas ($O_2$) molecules.

2. The method as specified in claim 1 wherein the poly-oxygenated aluminum hydroxide composition is administered intravenously.

3. The method as specified in claim 1 wherein the poly-oxygenated aluminum hydroxide composition comprises poly-oxygenated aluminum hydroxide particles having a diameter of less than or equal to 100 nm.

4. The method as specified in claim 1 wherein the poly-oxygenated aluminum hydroxide composition comprises poly-oxygenated aluminum hydroxide particles having a diameter of less than or equal to 1 um.

5. The method as specified in claim 1 wherein the poly-oxygenated aluminum hydroxide composition is a colloid solution with 10-25% addition of poly-oxygenated aluminum hydroxide.

6. The method as specified in claim 1 wherein the poly-oxygenated aluminum hydroxide composition is a crystalline solution with 10-25% addition of poly-oxygenated aluminum hydroxide.

7. The method as specified in claim 1 wherein the poly-oxygenated aluminum hydroxide composition has a concentration range of 0.1 mg/l to 1000 mg/l.

8. The method as specified in claim 1 wherein the poly-oxygenated aluminum hydroxide composition has poly-oxygenated aluminum hydroxide particles that are surface modified.

* * * * *